United States Patent
Yunker

(10) Patent No.: US 6,762,411 B2
(45) Date of Patent: Jul. 13, 2004

(54) RECONFIGURE LOCK FOR DUAL DETECTOR GAMMA CAMERA

(75) Inventor: David A. Yunker, Cicero, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 132 days.

(21) Appl. No.: 10/095,426

(22) Filed: Mar. 13, 2002

(65) Prior Publication Data

US 2003/0173521 A1 Sep. 18, 2003

(51) Int. Cl.$^7$ .............................................. G01T 1/166
(52) U.S. Cl. ........................ 250/363.05; 250/363.08; 250/363.02
(58) Field of Search ...................... 250/363.05, 363.08, 250/363.02

(56) References Cited

U.S. PATENT DOCUMENTS

| | | | | |
|---|---|---|---|---|
| 5,523,571 A | * | 6/1996 | Velazquez et al. | 250/363.05 |
| 5,866,906 A | * | 2/1999 | Jensen | 250/363.05 |
| 6,114,701 A | * | 9/2000 | Plummer et al. | 250/363.05 |

* cited by examiner

Primary Examiner—David Porta
Assistant Examiner—Christine Sung

(57) ABSTRACT

The present invention discloses a reconfigure lock for dual detector gamma camera that works with a triple race bearing. The outer race is stationary, it serves as part of the supporting frame. A detector (1) is mounted to the center race, which is driven by an integral gear. A detector (2) and the lock assembly are mounted to the inner race. The center and inner races rotate in unison when locked to one another.

8 Claims, 8 Drawing Sheets

RECONFIGURE LOCK FOR DUAL DETECTOR GAMMA CAMERA

BACKGROUND OF THE INVENTION

1. Field of the Invention

The present invention relates to a reconfigure lock for a dual detector in a gamma camera, for use in nuclear medicine.

2. Description of the Background Art

Gamma ray cameras are relatively well known devices used to detect gamma ray emissions from radioactive decay. A known gamma ray camera described in U.S. Pat. No. 3,011,057 for RADIATION IMAGE DEVICE, hereby incorporated by reference, uses a single sodium iodide ("NaI") scintillation detector crystal to detect gamma ray emissions. The detector crystal is positioned to receive a portion of the gamma ray emissions from the radioactive decay. When a gamma ray strikes and is absorbed in the detector crystal, the energy of the gamma ray is converted into a large number of scintillation photons that emanate from the point of the gamma ray's absorption in the detector. A photomultiplier tube, optically coupled to the detector crystal, detects a fraction of these scintillation photons and produces an electronic signal that is proportional to the number of detected incident scintillation photons. The gamma ray camera typically has several photomultiplier tubes placed in different positions, with the signals from the different photomultiplier tubes being combined to provide an indication of the positions and energies of detected gamma rays.

Gamma ray cameras are frequently used in nuclear medical imaging to record pictures of a radiation field emanating from a subject's body. The gamma rays originate from a decay of a radioactive tracer that has been introduced into the subject's body. The radioactive tracer, such as $^{99m}$Tc, is a pharmaceutical compound to which a gamma ray emitting nuclide has been attached and which undergoes some physiological process of interest after introduction into the body. For example, the tracer may accumulate in certain organs or tissues of interest, and thus provide an image of those organs or tissue.

Gamma ray cameras use detectors with a wide field of view to image the full width of the patient at each angular stop. Originally, gamma ray cameras used only one detector. This one detector was positioned above an organ that was to be imaged. This one detector was used for single photon emission computerized tomography (SPECT) or emission computerized tomography (ECT). SPECT and ECT require rotating the detector about the patient to obtain tomographic data and images. Technology then developed so that the gamma camera was passed over the entire body of the patient to obtain a complete image (whole body imaging).

Recent technological innovations in gamma ray cameras have produced dual detector systems in order to increase efficiency. These dual detector systems have their detector image director arrows oriented at a fixed angle of 180°. Having dual detector systems with the ability to have a fixed angle of 180° is very important so that the detectors can rotate about the patient only 180° rather than a full 360° rotation. For a total body scan, the detector is required to move along the entire length of the patient's body. The dual head system is more efficient because image data for both the anterior and posterior images can be obtained simultaneously. This can reduce the scan time up to one half. Reducing scan time reduces the cost of diagnosing the patient as well as reducing the time of patient discomfort. In addition, the system can be optimally configured by providing angular displacement between two detectors adjusted to any angle between 90° and 180°. Triple head systems have also been developed that have their image direction arrows oriented at fixed angles of 120°. Depending on the application, each of these cameras, (single, dual and triple), have certain features that are advantageous over another. Factors used to determine which system to use include the ability of the camera to perform the tasks, the quality of the images desired.

It is a goal of the present invention to present an improved method of a reconfigure lock for a dual detector gamma camera.

SUMMARY OF THE INVENTION

The present invention provides a reconfigure lock for a dual detector gamma camera with triple race bearing (outer, center and inner). The outer race serves as the supporting frame, the center race and inner races have the detectors mounted onto them. A lock assembly is mounted onto the inner race. The center and inner races rotate in unison when locked to one another. The center race has a separate locking segment for each individual configuration angle. The outward movement of the lock slide disengages it from the lock segment and engages it in the outer race pocket (locking pocket). When reconfiguration is complete, two switches (one in the lock and one in one of the segments) are closed.

DETAILED DESCRIPTION OF THE PREFERRED EMBODIMENT(S)

Figure 1:
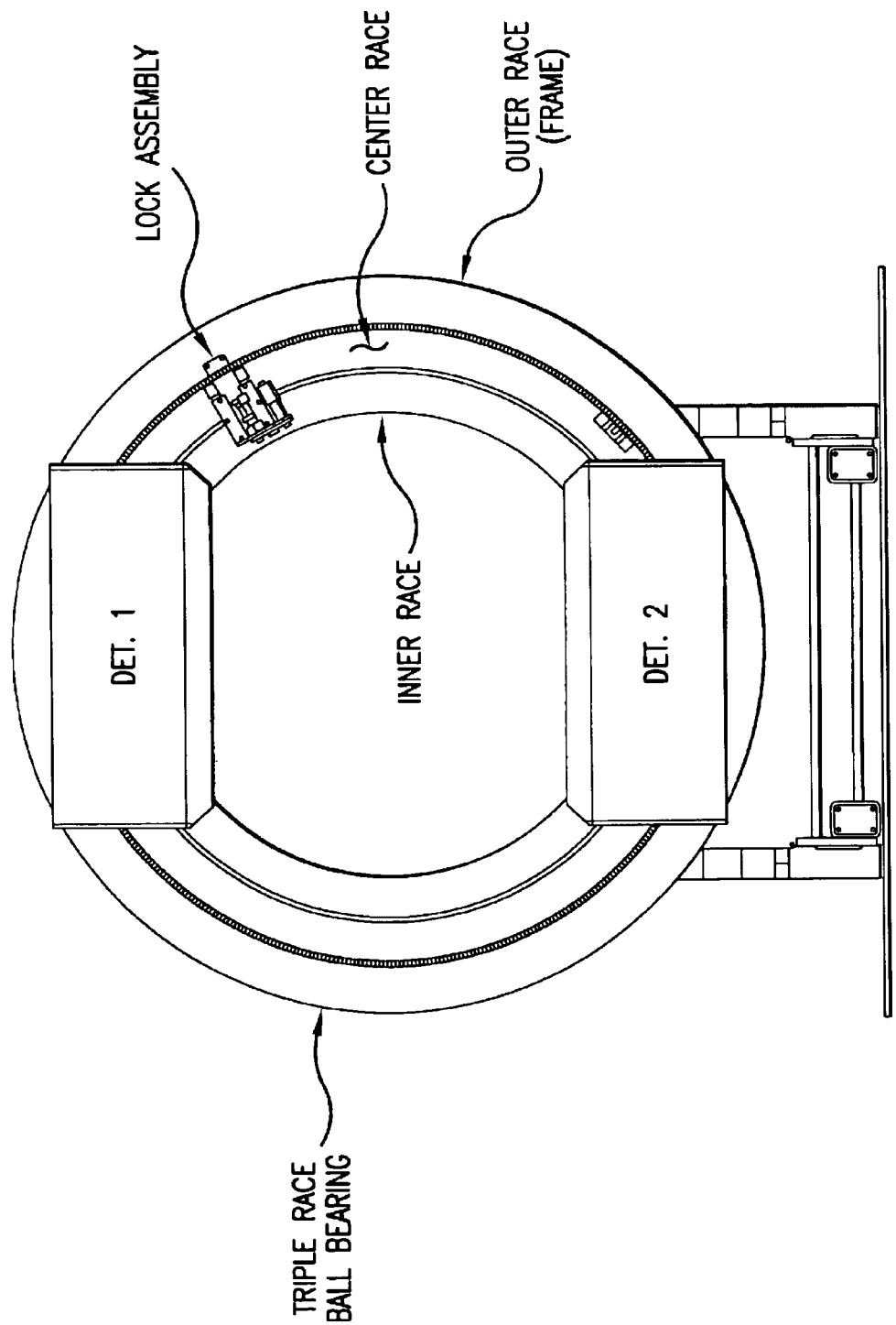
FIG. 1 is a triple race ball bearing reconfigure lock shown in the 180° configuration.
Figure 2:
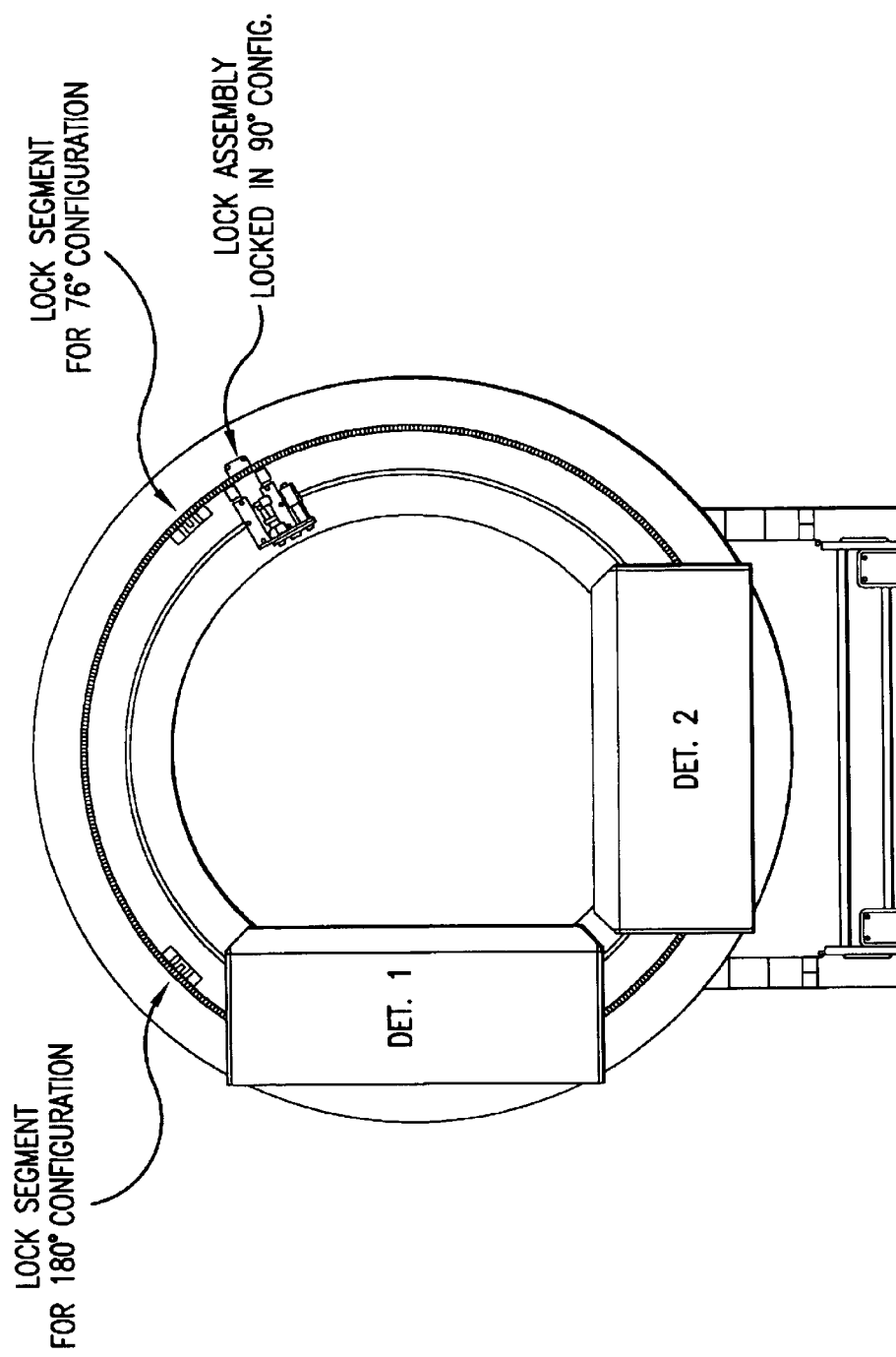
FIG. 2 is a triple race ball bearing reconfigure lock shown in the 90° configuration.

The reconfigure lock for dual detector gamma camera works with a triple race bearing. The outer race is stationary, it serves as part of the supporting frame. Detector 1 is mounted to the center race, which is driven by an integral gear (FIG. 1). Detector 2 and the lock assembly are mounted to the inner race. The center and inner races rotate in unison when locked to one another.

Figure 6:
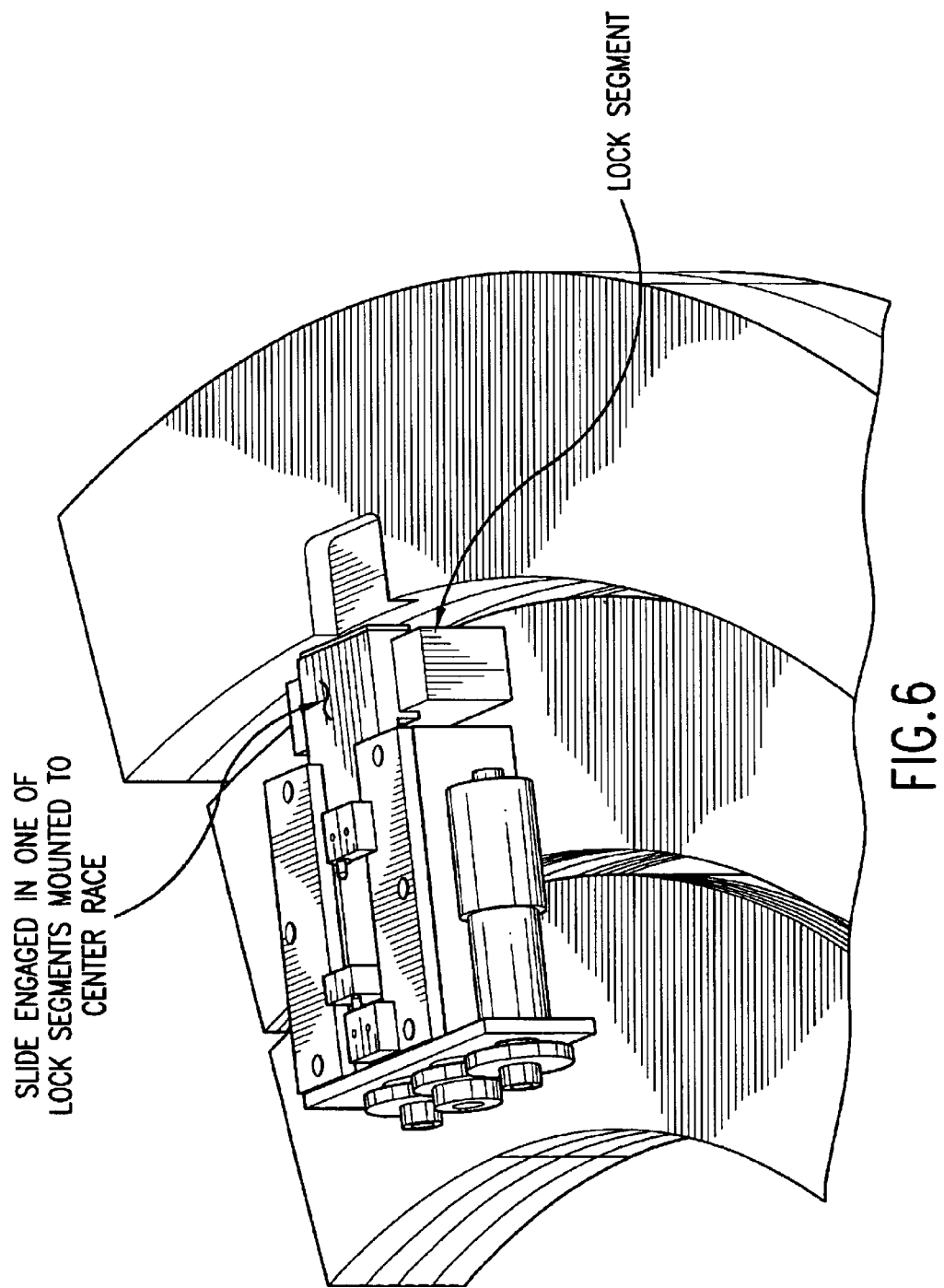
FIG. 6 is a view of the inner and center races locked.
Figure 7:
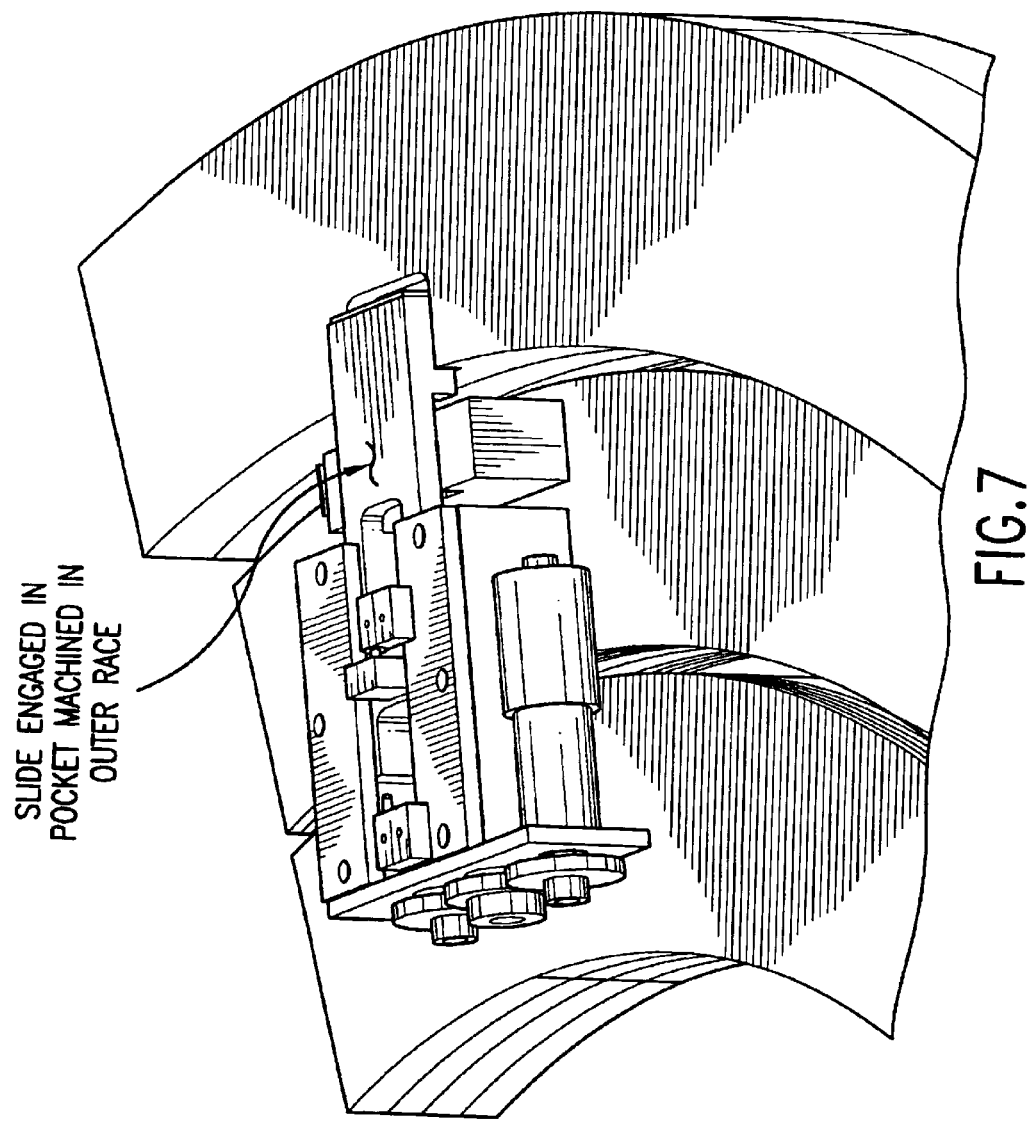
FIG. 7 is a view of the inner and outer races locked.
Figure 8:
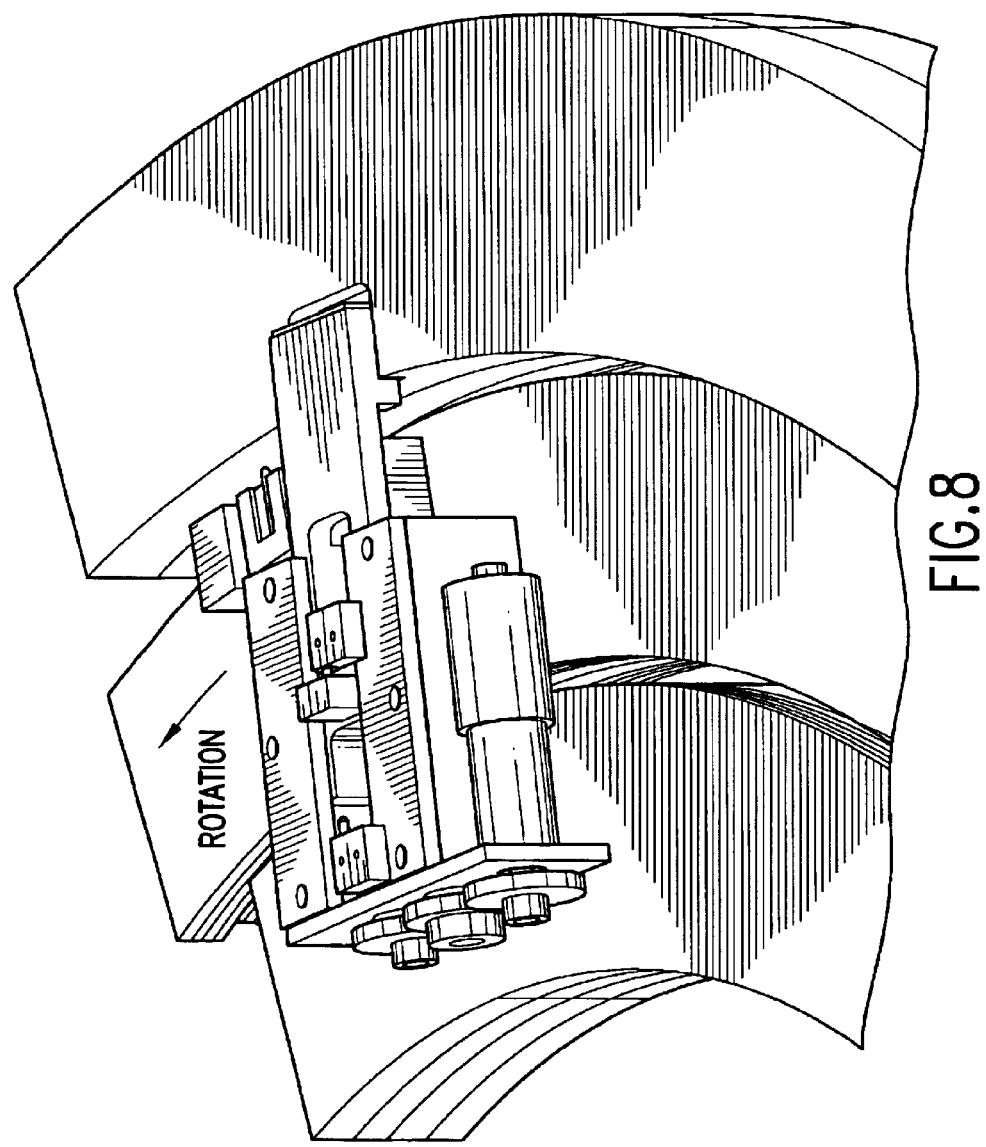
FIG. 8 is a view of the reconfiguration in process.

Reconfiguration of the lock is accomplished by rotating the center and inner races until Detector 2 is at 180° or the bottom dead center location. It is only at this position that the lock assembly aligns with a pocket in the outer race. The assembly makes it impossible for Detector 2 to be unlocked from Detector 1 at any position other than 180°. Since the detector is already at the bottom of the gantry, it cannot fall. The lock slide disengages from the lock segment mounted to the center race by outward movement of the lock slide. The lock slide then engages in the outer race pocket (locking pocket) (FIGS. 6 and 7). This engagement is accomplished with only one motion which is an improvement over previous inventions in the art. Now, the inner race and detector 2 are locked to the frame. The center race and detector 1 can be rotated on its own (FIG. 8).

Figure 3:
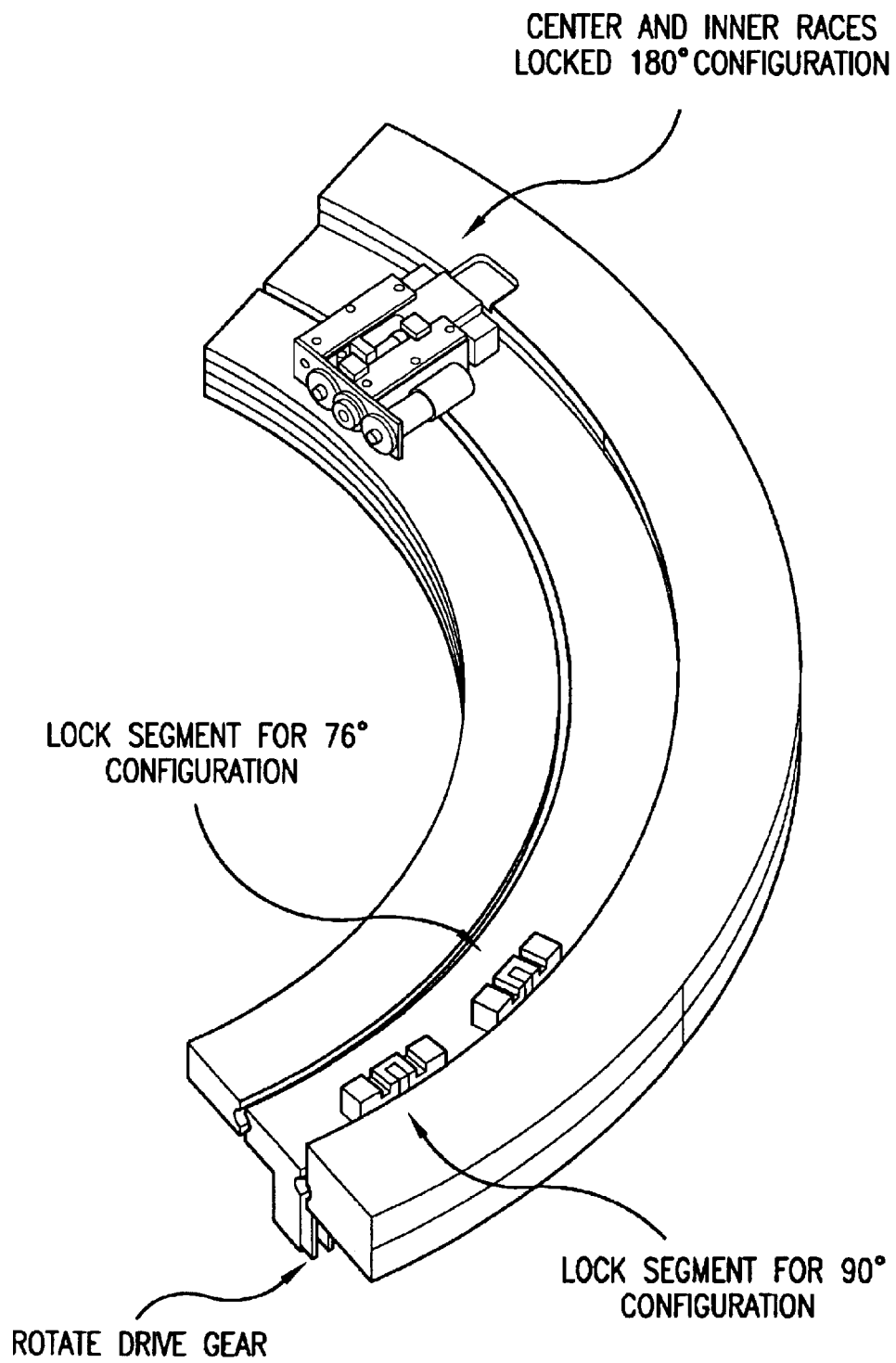
FIG. 3 is a view of the center race containing a separate locking segment for each individual configuration angle.

The center race contains a separate locking segment for each individual configuration angle (76°, 90°, 180°, etc., FIG. 3). Each segment also has its own micro-switch. This micro-switch closes when the lock closes. This provides indication of the exact configuration angle at all times, even upon power up.

Figure 4:
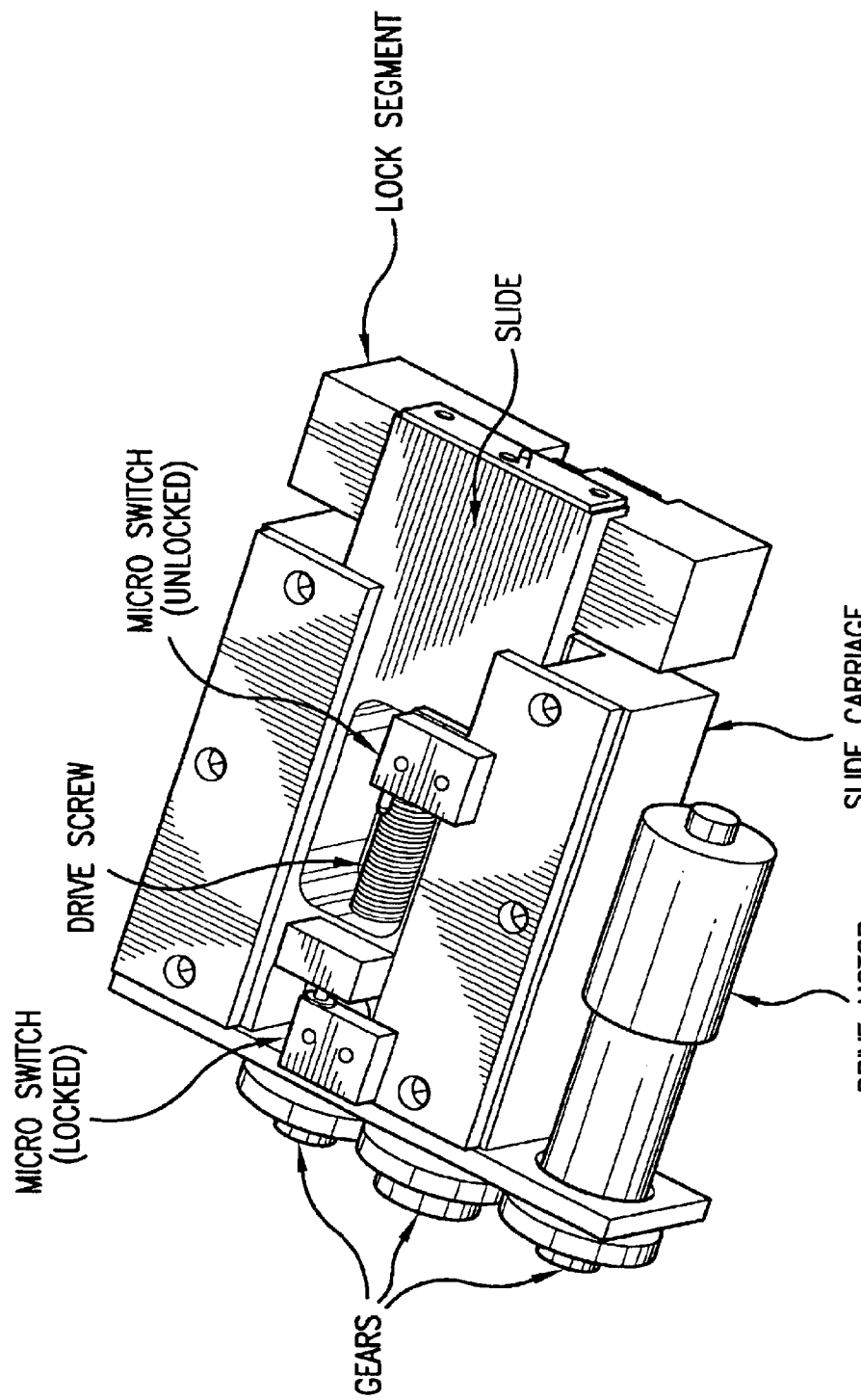
FIG. 4 is a top view of the lock assembly.
Figure 5:
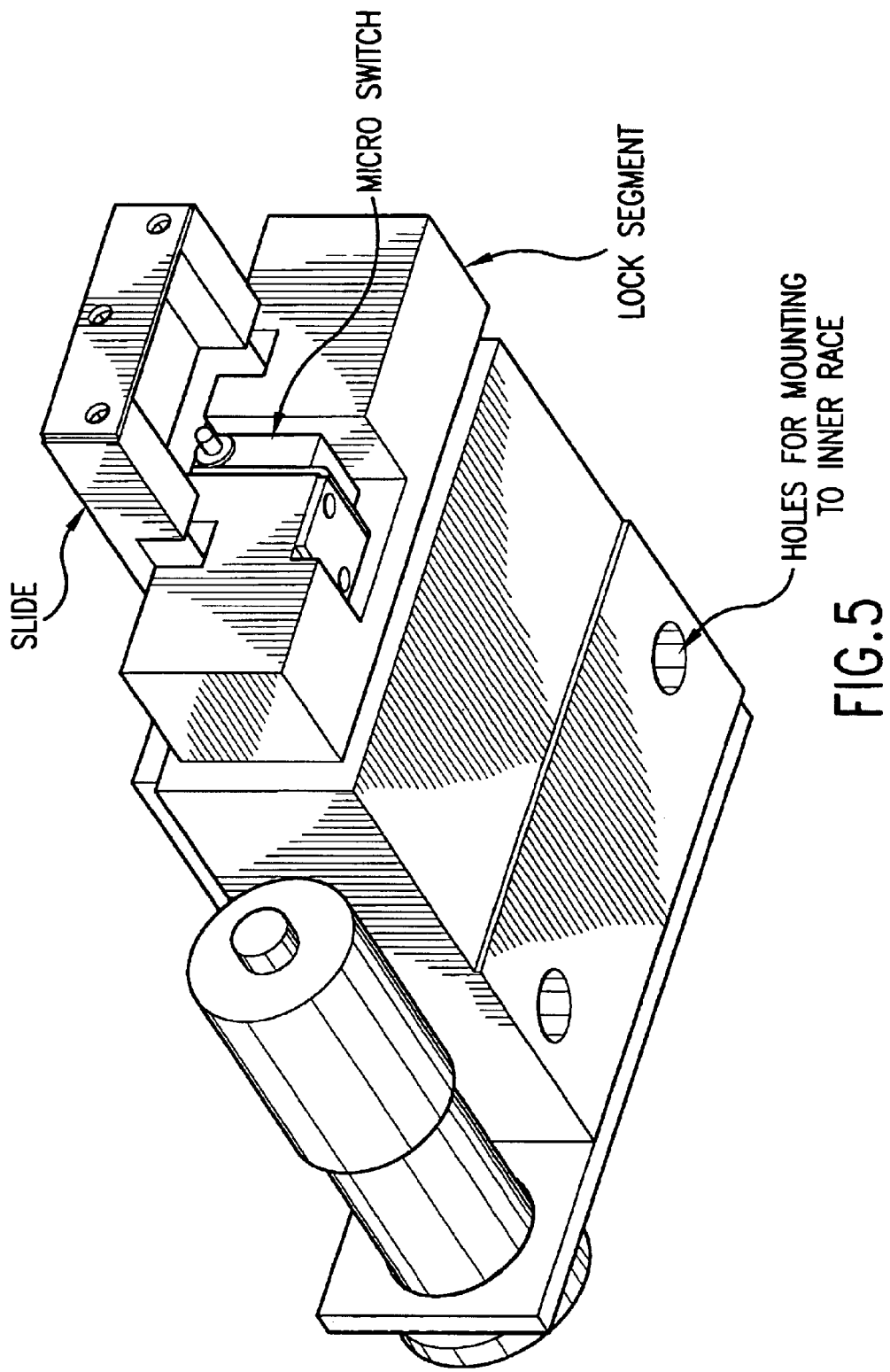
FIG. 5 is a bottom view of the lock assembly.

The lock assembly has two micro-switches, one for each position, open and closed (FIG. 4). When the lock slide is in transition, both switches are open. When reconfiguration is complete, two switches are closed, one in the lock and one in one of the segments. This redundancy offers an additional margin of safety. For normal operation, both switches must be closed.

What is claimed is:

1. A triple race bearing reconfigure lock for a dual detector gamma camera, comprising:
    a stationary race serving as a support frame;
    a first movable race having a first detector mounted thereon, said first movable race being coupled to said stationary race and being movable with respect to said stationary race;
    a second movable race having a second detector mounted thereon, said second movable race being coupled to said first movable race and being movable with respect to said first movable race;
    a lock assembly mounted on said second movable race;
    a plurality of lock segments mounted on said first movable race, each of said plurality of lock segments being positioned at a location on said first movable race corresponding to a different configuration angle for configuring the relative orientation between said first and second detectors;
    a locking pocket formed in said stationary race;
    said lock assembly having a slide mechanism containing a channel, said slide mechanism being movable outward from said lock assembly to a first extended position spanning said first movable race, wherein said slide mechanism engages with said locking pocket in said first extended position allowing said lock segments to be rotated through said channel; and
    said slide mechanism being movable inward toward said lock assembly to a second retracted position wherein said channel is retracted such that said slide mechanism engages with one of said lock segments and prevents said engaged lock segment from rotating with respect to said slide mechanism when said one of said lock segments is aligned with said slide mechanism.

2. The reconfigure lock of claim 1, further comprising a pair of microswitches located on said lock assembly, such that a first of said pair of microswitches is closed when said slide mechanism is in said first position, and a second of said pair of microswitches is closed when said slide mechanism is in said second position, as an indication of whether said first and second movable races are locked in unison or not.

3. The reconfigure lock of claim 1, further comprising a microswitch located on each of said plurality of lock segments, such that a microswitch of an aligned lock segment is closed when said slide mechanism is in said second position, and microswitches of said plurality of lock segments are open when said slide mechanism is in said first position, as an indication of whether said first and second movable races are locked in unison or not.

4. The reconfigure lock of claim 2, further comprising a microswitch located on each of said plurality of lock segments, such that a microswitch of an aligned lock segment is closed when said slide mechanism is in said second position, microswitches of said plurality of lock segments are open when said slide mechanism is in said first position, as an indication of whether said first and second movable races are locked in unison or not, and operation of said detector system is disabled unless said second microswitch of said pair of microswitches and one microswitch of a lock segment are closed.

5. A triple race bearing reconfigure lock for a dual detector gamma camera, comprising:
    a stationary race serving as a support frame;
    a first movable race having a first detector mounted thereon, said first movable race being coupled to said stationary race and being movable with respect to said stationary race;
    a second movable race having a second detector mounted thereon, said second movable race being coupled to said first movable race and being movable with respect to said first movable race;
    a lock assembly mounted on said second movable race;
    a plurality of lock segments mounted on said first movable race, each of said plurality of lock segments being positioned at a location on said first movable race corresponding to a different configuration angle for configuring the relative orientation between said first and second detectors;
    a locking pocket formed in said stationary race;
    said lock assembly engaging with said locking pocket in a first extended position allowing said first movable race to be rotated between said stationary race and said second movable race; and
    said lock assembly engaging with one of said lock segments in a second retracted position, thereby locking said first movable race in position with respect to said second movable race and allowing said first and second movable races to be rotated in unison with respect to said stationary race.

6. The reconfigure lock of claim 5, further comprising a pair of microswitches located on said lock assembly, such that a first of said pair of microswitches is closed when said lock assembly is in said first position, and a second of said pair of microswitches is closed when said lock assembly is in said second position, as an indication of whether said first and second movable races are locked in unison or not.

7. The reconfigure lock of claim 5, further comprising a microswitch located on each of said plurality of lock segments, such that a microswitch of a lock segment is closed when said lock assembly is engaged therewith, and microswitches of said plurality of lock segments are open when said lock assembly is in said first position, as an indication of whether said first and second movable races are locked in unison or not.

8. The reconfigure lock of claim 6, further comprising a microswitch located on each of said plurality of lock segments, such that a microswitch of a lock segment is closed when said lock assembly is engaged therewith, microswitches of said plurality of lock segments are open when said lock assembly is in said first position, as an indication of whether said first and second movable races are locked in unison or not, and operation of said detector system is disabled unless said second microswitch of said pair of microswitches and one microswitch of a lock segment are closed.

* * * * *